(12) United States Patent
Swarvar et al.

(10) Patent No.: US 11,832,027 B2
(45) Date of Patent: *Nov. 28, 2023

(54) VISUAL ANALYSIS PILL DISPENSER

(71) Applicant: ARxIUM, Inc., Buffalo Grove, IL (US)

(72) Inventors: Aaron C. Swarvar, Hudsonville, MI (US); Jacob A. Dent, Wildwood, IL (US); Gabriel V. Taut, Highland Park, IL (US); Thomas E. Doherty, Winnipeg (CA)

(73) Assignee: ARxIUM, Inc., Buffalo Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/681,366

(22) Filed: Feb. 25, 2022

(65) Prior Publication Data
US 2022/0180996 A1 Jun. 9, 2022

Related U.S. Application Data

(63) Continuation of application No. 17/097,475, filed on Nov. 13, 2020, now Pat. No. 11,295,843, which is a
(Continued)

(51) Int. Cl.
*H04N 7/18* (2006.01)
*G16H 20/13* (2018.01)
(Continued)

(52) U.S. Cl.
CPC ............. *H04N 7/183* (2013.01); *A61J 7/0076* (2013.01); *A61J 7/02* (2013.01); *G06F 18/22* (2023.01);
(Continued)

(58) Field of Classification Search
CPC ....... G16H 20/13; G16H 70/40; A61J 7/0076; A61J 7/02; A61J 2200/70; A61J 2205/20; A61J 2205/60; A61J 2205/50; A61J 2205/40; G06K 9/6201; H04N 5/77; H04N 7/183; G06T 7/0002
See application file for complete search history.

(56) References Cited

U.S. PATENT DOCUMENTS 4,847,764 A * 7/1989 Halvorson ........... G06Q 10/087 700/231
6,155,454 A 12/2000 George et al.
(Continued)

*Primary Examiner* — Fernando Alcon
(74) *Attorney, Agent, or Firm* — Reinhart Boerner Van Deuren s.c.

(57) ABSTRACT

This disclosure provides a visual analytical method of verifying dispensed pills. In a preferred embodiment, a camera captures one or more parameters of each pill as it travels along a dispense path. The camera stores the parameters, and a processor displays the parameters or evaluates whether the parameters are within a threshold limit for the dispensed pill. If the parameter is outside the threshold, the pill or the receptacle is separated and/or removed. If all the parameters are within the threshold, the pill is stored in a receptacle, and the images are processed and archived for future verification. The process is repeated for each pill in the dispenser. The system captures at least one verification image for every pill dispensed into the receptacle.

20 Claims, 5 Drawing Sheets

Related U.S. Application Data continuation of application No. 16/524,545, filed on Jul. 29, 2019, now Pat. No. 10,872,688.

(60) Provisional application No. 62/711,960, filed on Jul. 30, 2018.

(51) Int. Cl.
| | |
|---|---|
| *G16H 70/40* | (2018.01) |
| *H04N 5/77* | (2006.01) |
| *A61J 7/02* | (2006.01) |
| *A61J 7/00* | (2006.01) |
| *G06F 18/22* | (2023.01) |

(52) U.S. Cl.
CPC ............ *G16H 20/13* (2018.01); *G16H 70/40* (2018.01); *H04N 5/77* (2013.01); *A61J 2200/70* (2013.01); *A61J 2205/20* (2013.01); *A61J 2205/40* (2013.01); *A61J 2205/50* (2013.01); *A61J 2205/60* (2013.01)

(56) References Cited

U.S. PATENT DOCUMENTS

| | | | | |
|---|---|---|---|---|
| 8,145,353 | B1* | 3/2012 | Cotner | G07F 17/0092 |
| | | | | 700/242 |
| 10,512,592 | B1* | 12/2019 | Sandhu | G07F 11/005 |
| 10,669,098 | B1* | 6/2020 | Terzini | B65B 35/10 |
| 10,984,901 | B1* | 4/2021 | Locklear | G07F 11/52 |
| 10,998,094 | B1* | 5/2021 | Chiu | G16H 20/13 |
| 11,373,745 | B1* | 6/2022 | Heaps | G16H 40/67 |
| 11,428,648 | B2* | 8/2022 | Ursella | G06T 7/74 |
| 11,464,711 | B2* | 10/2022 | Provencher | A61J 7/0481 |
| 2001/0027634 | A1 | 10/2001 | Hebron et al. | |
| 2001/0041968 | A1 | 11/2001 | Hamilton | |
| 2004/0104241 | A1 | 6/2004 | Broussard et al. | |
| 2005/0152029 | A1 | 7/2005 | Endo | |
| 2005/0187791 | A1 | 8/2005 | DiMaggio et al. | |
| 2007/0023444 | A1 | 2/2007 | Holloway et al. | |
| 2008/0319795 | A1* | 12/2008 | Poteet | G16H 70/40 |
| | | | | 705/2 |
| 2010/0131097 | A1* | 5/2010 | Young | G01N 21/9508 |
| | | | | 700/244 |
| 2011/0119073 | A1 | 5/2011 | Hanina et al. | |
| 2011/0297590 | A1 | 12/2011 | Ackley et al. | |
| 2012/0232693 | A1* | 9/2012 | Allinson | G07F 17/0092 |
| | | | | 700/237 |
| 2012/0330684 | A1* | 12/2012 | Jacobs | G07F 11/005 |
| | | | | 604/404 |
| 2013/0197693 | A1 | 8/2013 | Kamen et al. | |
| 2013/0279774 | A1* | 10/2013 | Helgason | A61J 7/0084 |
| | | | | 382/128 |
| 2013/0314535 | A1 | 11/2013 | Yuyama et al. | |
| 2015/0070485 | A1 | 3/2015 | Kim | |
| 2015/0286798 | A1 | 10/2015 | Weber | |
| 2015/0302255 | A1* | 10/2015 | Gershtein | G06V 10/42 |
| | | | | 382/128 |
| 2016/0163034 | A1 | 6/2016 | Jacobs et al. | |
| 2017/0085756 | A1 | 3/2017 | Thomas et al. | |
| 2017/0140601 | A1 | 5/2017 | Kohama et al. | |
| 2017/0224585 | A1* | 8/2017 | Jacobs | H04N 7/183 |
| 2018/0091745 | A1* | 3/2018 | Holmes | H04N 5/2256 |
| 2018/0333335 | A1* | 11/2018 | Carson | A61J 7/0076 |
| 2019/0050660 | A1 | 2/2019 | Iwami | |
| 2019/0107501 | A1 | 4/2019 | Mehregany | |
| 2020/0035345 | A1* | 1/2020 | Swarvar | A61J 7/02 |
| 2020/0066388 | A1 | 2/2020 | Kamen et al. | |
| 2020/0175317 | A1* | 6/2020 | Iwami | G06T 7/00 |
| 2020/0175319 | A1* | 6/2020 | Yokouchi | G06T 5/003 |
| 2020/0253828 | A1 | 8/2020 | Mathew | |
| 2020/0411158 | A1* | 12/2020 | Iwami | A61J 3/00 |
| 2021/0059903 | A1* | 3/2021 | Crowley | G06F 21/32 |
| 2021/0086934 | A1* | 3/2021 | Burkett, Jr. | B65B 59/04 |
| 2022/0139519 | A1* | 5/2022 | Schilling | G06Q 30/016 |
| | | | | 705/2 |

\* cited by examiner

VISUAL ANALYSIS PILL DISPENSER

CROSS-REFERENCE TO RELATED PATENT APPLICATIONS

This application is a continuation of U.S. Non-Provisional application Ser. No. 17/097,475, filed Nov. 13, 2020, which is a continuation of U.S. Non-Provisional application Ser. No. 16/524,545, now U.S. Pat. No. 10,872,688, filed Jul. 29, 2019, which claims the benefit of and priority to U.S. Provisional Application No. 62/711,960, filed Jul. 30, 2018, which is incorporated herein by reference in its entirety.

BACKGROUND OF THE INVENTION

The present disclosure generally relates to the field of pill dispensers. The present disclosure relates specifically to a system and method of verifying dispensed pills.

Pharmacists are responsible for ensuring that the pills dispensed to a patient are the pills prescribed by the physician. When pills are automatically dispensed into a container, the container is later reviewed by a Pharmacist, but only a small sample of the contents is visible which often results in a random sample of dispensed pills being compared to the features of the prescribed pill as the Pharmacist is not able to review each dispensed pill.

SUMMARY OF THE INVENTION

One embodiment of the disclosure relates to a visual analysis validation system. The visual analysis system includes a dispense path, a camera, a processor, a receptacle and a display. The dispense path dispenses medical products with visible parameters characteristic of the medical product. The dispense path moves the medical products toward the receptacle. The camera is supported about the dispense path and records signals representative of the medical product parameters. The processor receives the recorded signals from the camera and generates and stores the recorded signal indicative of the medical product parameters. The processor stores the recorded signal associated with the parameter of the medical product. The receptacle receives the dispensed medical products associated with the recorded signals indicative of parameters.

The display provides a visual representation of the recorded signal that is indicative of the parameters for each dispensed medical product. The display also indicates the number of medical products dispensed into the receptacle.

Another embodiment of the disclosure relates to a pill dispenser. The pill dispenser includes a dispenser, a camera, a receptacle, a processor, and a display. The dispenser couples to a hopper that stores pills. The dispenser includes a dispense path though which pills move from the hopper to the receptacle. The camera is supported about the dispense path and provides a light path from the dispensed pills to the camera. The camera generates indicia signals that are representative of the pill parameters of each dispensed pill. The receptacle collects the dispensed pills with the associated recorded pill parameters. The processor receives the indicia signals from the camera and compares the indicia signals of the pill parameter to a threshold for the dispensed pill. The processor stores the pill parameter threshold data associated with the receptacle. The processor generates diversion signals for the receptacle when the indicia signals in the receptacle represent pill parameters outside the threshold. The display represents the diversion signal from the processor and generates an image indicative of the pill parameters outside the threshold and dispensed into the receptacle.

Another embodiment of the disclosure relates to a pill dispenser. The pill dispenser includes a hopper, a dispenser, a pill separator, a camera, a processor, and a receptacle. The hopper stores pills to be dispensed into the receptacle. Each pill has visible indicia of at least one characteristic pill parameter of the pill. The dispenser includes a dispense path though which pills move from the hopper towards the receptacle. The pill separator is coupled to the dispense path and diverts pills from the dispense path in response to a diversion signal. The camera is supported about the dispense path and provides a vision path from pills to the camera. The camera generates indicia signals that are representative of the visible indicia of the pill and/or pill parameters. The processor coupled to the pill separator and the camera that receives indicia signals from the camera, generates and stores pill characteristic data in association with a time of the associated indicia signals, and applies diversion signals to the pill separator such that the pill separator diverts pills from the dispense path in response to the diversion signals. The processor generates diversion signals when the indicia signals represent a characteristic outside a predetermined tolerance of the distributed pill, which requires diversion of the pill from the dispense path. The receptacle collects each pill with recorded pill parameters that are within the tolerance.

Alternative exemplary embodiments relate to other features and combinations of features as may generally be recited in the claims.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION

Figure 1:
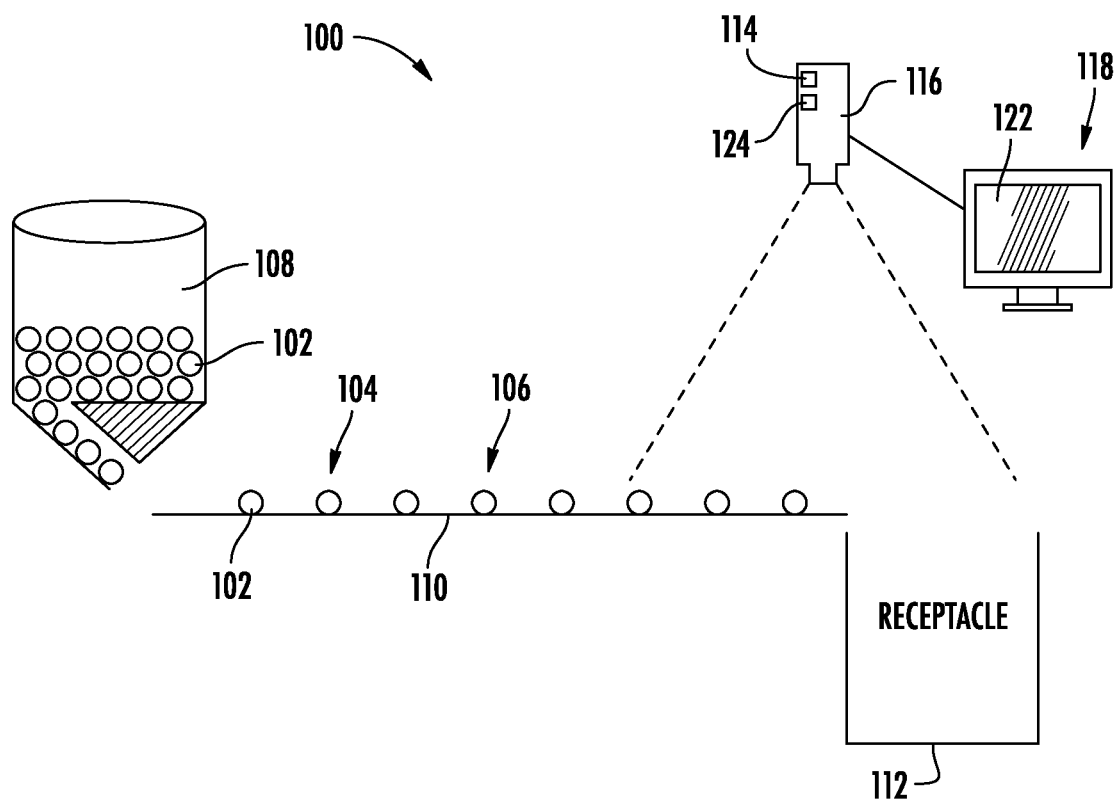
FIG. 1 is a pill dispensary system that records characteristic parameters of dispensed pills in real-time, according to an exemplary embodiment.

The figures generally illustrate various embodiments of a pill dispenser. Pill dispensers generally involve separating pills from a hopper that stores a large capacity of pills into a plurality of receptacles that each hold a relatively smaller number of pills. Once the separation has taken place, a verification process begins. A human (e.g., a pharmacist) must verify that the dispensed pills in the receptacle match the dispensed pills in the hopper and that the prescribed dose and quantity are accurate. In practice, a National Drug Code (NDC) identifies the manufacturer of the pill and the dose. In one embodiment, the pill dispenser system uses the unique NDC number to identify pill parameters (e.g., a batch of pills stored in the hopper). For example, the unique NDC identification for a batch of pills identifies pill parameters such as the size, shape, color, dose, and/or other marks (e.g., characteristics of the pill). A database stores the correlations between the pill parameters and the unique NDC identifier to retrieve them for future use and identify the distributed pills. For example, two manufacturers can create the same pill with the same medication and dose, but with different pill parameters. The unique NDC identifier provides a different unique code for each pill manufacturer and each pill. Thus, the database correlates the pertinent pill parameters for a pill with the unique NDC identifier for classification of the pill. In this way, the NDC identify can identify the pill and tolerance values for the pill parameters of the pill in the database.

Using the pill parameters, a pill dispenser system distributes pills from the hopper to the receptacle with selected parameters. The characteristic parameters have a tolerance or threshold to distinguish from pills that do not have the required parameters. For example, a pill dispensary system uses a threshold (e.g., a tolerance) for each pill parameter to identify and/or separate dispensed pills within the threshold from dispensed pills outside the threshold The system of the present disclosure allows for visual inspection of pills in a dispenser to record and archive each pill dispensed into a receptacle. This process visually records one or more images of pertinent pill parameters for verification and audit purposes. In some embodiments, the system automatically removes or isolates a pill if a single pill parameter is outside the threshold.

In some embodiments, the system assigns a batch number to the pills in the receptacle corresponding to an image for each dispensed pill in the receptacle. Once dispensed, the system records and stores the verification images for the contents of the receptacle (e.g., pills) associated with the receptacle and renders images that are accessible for review at a later time. In some embodiments, the visual record provides a flag for parameters at or near the threshold, and later review of the visual record provides verification. This process ensures more accurate dispensing of pills and enables documented evidence of the content for each receptacle. Another benefit of the system is the ability to separate the verification process. For example, the system permits the pharmacist to relocate to a remote site and verify the pills dispensed into the receptacle. This feature enhances the pharmacist's ability to verify each pill and enables pharmacists to verify pills at various remote locations. For example, a pharmacist works from home to verify the pills deposited into each receptacle.

FIG. 1 illustrates a medical product visualization system or pill dispenser system 100 that enables verification of the quality and quantity of dispensed pills 102. Pill 102, as used in this disclosure, is construed broadly to include any medical product subject to visual verification controls. For example, any medical product subject to visual or electromagnetic inspection of the quantity and quality of the product is termed a "pill" for purposes of this disclosure. Each pill 102 includes characteristic pill parameters 104 (e.g., visible indicia) that identify the pill 102. System 100 identifies the pill parameters 104 on a dispense path or channel 106 that is configured to orient and/or move pills 102. System 100 includes a hopper 108 to store pills 102 and a dispenser 110 with channel 106 that orients pills 102. For example, channel 106 includes any dispense path for transporting pills 102 from hopper 108 to a receptacle 112. For example, dispense path or channel 106 may include dropping pills 102 from hopper 108 directly in receptacle 112. Channel 106 may include a vibratory dispense path, a track, a slide or inclined plane, a lever, or a free fall that transports pills 102 from hopper 108 to receptacle 112.

A processor 114 stores, analyses, and/or sends signals indicative of the pill parameters 104 of each pill 102. To capture this data, a camera 116 is supported near channel 106 to capture and/or record data signals (e.g., images 118) representative of pill parameters 104. Camera 108 generates indicia signals or images 118 representative of the characteristic pill parameters 104, which assist a human or automated system to determine whether each pill 102 meets the threshold criteria. As used herein, image 118 is interpreted broadly and includes data, visual indicia, indicia signals, and/or a photographic or video image 118 (e.g., a single photographic "frame" of a video image). The image 118 is generated by camera 116 and processed and/or stored by processor 114.

FIG. 1 illustrates a pill dispenser system 100 that assists a pharmacist or machine to quickly identify receptacles 112 with at least one pill 102 that is outside a threshold. In contrast to FIG. 2, FIG. 1 does not include a separator 220. Instead of automating the separation process, the system 100 uses camera 116 to send signals or images indicative of pill parameters 104 for each pill 102 dispensed in a receptacle 112. In some embodiments, an operator (e.g., pharmacist) views the pill parameters 104 on a display 118 to validate or verify receptacle 112 contents.

As will be discussed in greater detail below, processor 114 can store the pill parameters 104 for visual review by a human (e.g., a pharmacist), or use post-processing to automatically identify receptacles 112 with a distributed pill 102 that has pill parameters 104 outside the threshold. In this embodiment, if processor 114 determines that the pill parameters 104 exceed the threshold, processor 114 sends a separation or diversion signal for the receptacle 112 associated with the pill 102. Later, a human, such as a pharmacist, sorts through pills 102 in receptacle 112 to find pill(s) 102 that do not conform or exceed the threshold limit. Thus, separation of non-conforming pills 102 that exceed the threshold may be automated or manual.

In an automated process that removes pills 102 with pill parameters 104 outside the threshold, an operator or pharmacist may still review the separated pills 102 contained in a separate container and/or pills 102 dispensed into receptacle 112 to verify, dispose, and/or recycle the separated pills 102. Alternatively, physical analysis may determine that pills 102 were incorrectly separated and return pills 102 to hopper 108 for future use. In some embodiments, separator 220 removes pill 102 from dispenser 110 for additional analysis (e.g., by a separate camera 116 with advanced photo-rendering) and returns pill 102 to dispenser 110 or receptacle 112 when it more accurately determines pill parameters 104 relative to the threshold.

Figure 2:
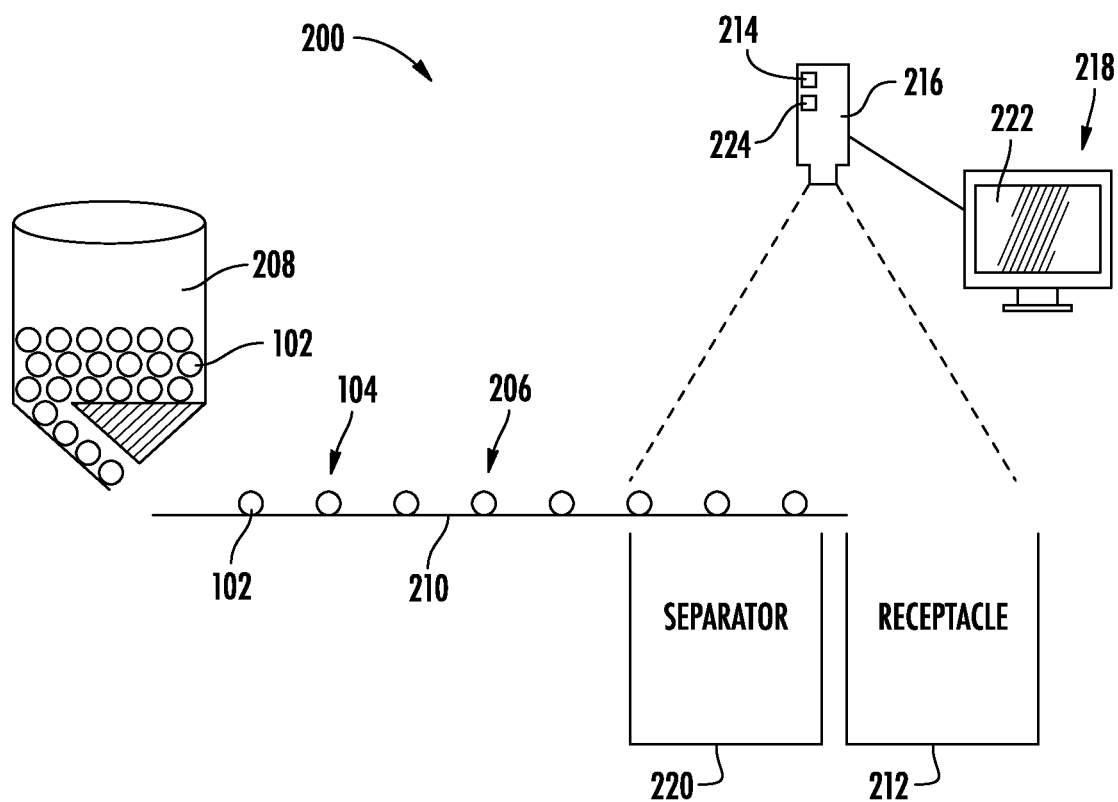
FIG. 2 is the pill dispensary system of FIG. 1 with a separator, the system records dispensed pills and separates them into a separator or a receptacle in real-time based on diversion indicia signals, according to an exemplary embodiment.

As shown in the embodiment of FIG. 2, if pill parameters 104 for pill 102 are outside threshold values or tolerance criteria, a pill separator 220 ("separator 220") that is coupled to channel 106 removes or diverts pill 102 from reaching dispenser 210 in response to a diversion signal (e.g., from processor 214). For example, when a pill parameter 104 is outside a threshold or tolerance, separator 220 diverts pill 102 from dispense path 206 and consequently away from receptacle 212. In this configuration, processor 214 performs and automates the threshold pill parameter 104 analysis to determine whether to remove (e.g., with separator 220) or dispense the pill 102 from dispense path 206 into receptacle 212. In some embodiments, dispensed pills 102 in receptacle 212 are sold directly to a patient.

As shown in FIG. 1, system 100 further includes a display 122 to review images 118 (e.g., data signals and/or visual indicia) of pills 102 in channel 106 and captured by camera 116. System 100 stores images 118 in memory 124 (e.g., for future retrieval). Pill dispenser system 100 enables verification of dispensed pills 102 in real time and/or through post-processing. In addition, system 100 enables time-delay of the visual analysis. For example, if pills 102 are dispensed faster than the pharmacist's ability to visually inspect each pill 102, system 100 enables the pharmacist to inspect all the dispensed pills 102 at a predetermined or at-will rate.

In some embodiments, system 100 includes hopper 108 that stores a batch or load of pills 102 in bulk. Each pill 102 includes at least one characteristic pill parameter 104. In other embodiments, system 100 is configured to work with a preexisting hopper 108. The operator identifies pills 102 in hopper 108 according to an identification number assigned by the National Drug Code (NDC). For example, the NDC correlates pill parameters 104 with a threshold for a standard size, profile, shape, color, dose, markers, and/or other identifying pill parameters 104 for the particular pill 102. System 100 separates pills 102 in hopper 108 into one or more receptacles 112. For example, hopper 108 contains a batch of 10,000 pills 102 for distribution to three hundred thirty-three (333) receptacles 112 (e.g., 30 pills in each receptacle 112). In some embodiments, hopper 108 dispenses pills 102 at a fixed rate. For example, hopper 108 dispenses 5 pills 102 per second. In various embodiments, hopper 108 dispenses more than 10 pills per second, 15 pills per second, 20 pills per second, 25 pills per second, 30 pills per second or more.

In some embodiments, hopper 108 correlates an NDC to a batch code (e.g., a unique batch code that identifies the batch of pills dispensed with the NDC for pill 102). For example, the batch code includes the NDC number appended by a load number for hopper 108 and a group number for receptacle 112. Each hopper 108 includes an NDC number and load number, such that the first load is assigned a different number than the second load. In some embodiments, the system 100 assigns sequential load numbers, such that the first load is assigned a load number of one (0001), the second a load number of two (0002), etc. For example, the first receptacle 112 receives a group number of one (0001) for the first group dispensed, the second receptacle 112 batch receives a group number of two (0002), and so forth. In this way, the first unique batch number (0001) assigned to the first receptacle 112 is different from the second unique batch number (0002) assigned to the second receptacle 112. In some embodiments, the batch number combines the load number and group number to uniquely identify pills 102 dispensed from hopper 108 and the specific group of pills 102 distributed to receptacle 112. In some embodiments, system 100 assigns a unique load number and/or group number to hopper 108 and/or receptacle 112, respectively. For example, hopper 108 has an identifying load number and receptacle 112 has an identifying group number. In some embodiments, system 100 appends these numbers to the NDC identifier (e.g., on receptacle 112) and/or assigns unique numbers to each batch and load, which identify the NDC identifier. By assigning unique (either sequential or random) batch codes that identify the load (e.g., the hopper 108 load) and group (e.g., the receptacle group) of pills 102, the system 100 stores and retrieves images 118 of each pill 102 associated with receptacle 112 of each group assigned to that batch code.

A dispenser 110 couples to hopper 108 and orients pills 102 to show pill parameters 104 and dispenses pills 102 within a threshold into receptacle 112. Channel 106 of dispenser 110 moves pills 102 from hopper 108 toward receptacle 118. Dispenser 110 operates to orient pills 102 so that the verification system 100 (e.g., camera 116) can identify one or more pill parameters 104 on each dispensed pill 102.

In some embodiments, dispenser 110 transports pills 102 in a fixed direction at a fixed rate. For example, dispenser 110 transports 10,000 containers (e.g., of thirty pills each or 300,000 pills/8 hours). In this fixed rate system, dispenser 110 transports approximately 10.4 pills/second. Alternatively, dispenser 110 may transport pills 102 in different directions and/or at different rates through system 100. In some embodiments, dispenser 110 fills at least 500 containers of thirty pills each in an 8 hour day (e.g., 15,000 pills/8 hrs or 0.52 pills/sec). For example, dispenser 110 transports pills 102 with known pill parameters 104 along system 100 at a fixed rate in at least one section of system 100. By similarly orienting each pill 102 on channel 106, identifying pill parameters 104 consistently remain visible and are captured by camera 116.

In some embodiments, camera 114 utilizes photo-rendering techniques to enhance images 118 of pill parameters 104. For example, dispenser 110 alters the lighting, speed, and/or temperature at or near dispense path 104 and/or camera 116 so that images 118 of pills 102 better identify pill parameters 104. Dispenser 110 may orient pills 102 in a variety of different configurations. For example, dispenser 110 orients pills 102 in the channel 106 by placing pills 102 in an equally spaced but arbitrary orientation relative to a top, bottom, and/or side of pill 102. In another example, dispenser 110 orients pills 102 in channel 106 so that pill parameters 104 (including marks on pills 102, e.g., the dose, such as 100 mg) remain visible to camera 116. Dispenser 110 operates to orient pills 102 in a known configuration along channel 106 that transports pills 102 through system 100 at a known and/or predetermined rate.

In some embodiments, dispenser 110 includes a vibratory tray or dispenser path along channel 106 to orients pills 102 so that each pill 102 has a consistent orientation and/or configuration. In some embodiments, the speed of channel 106 determines the rate pills 102 pass camera 116 and dispenser 110 evenly spaces each pill 102 along channel 106. In some embodiments, a robot places pills 102 along channel 106 in a consistent orientation and distance. Other embodiments include dropping pills 102 into a tray configured to receive and orient pill 102 or driving a belt with pockets to orient pills 102 in dispenser 110. For example, the tray orients and receives a single pill 102 in each pocket of the belt. In some embodiments, pills 102 fall through an open chute into dispenser 110. In this configuration, dispenser 110 includes an open chute for camera 116 to capture pill parameters 104 for pills 102 as they fall through the air, e.g., a light or laser is directed at falling pills 102. The laser visually counts pills 102 and/or captures pill parameters 104 in photo/video images 118 as pills 102 fall through the open chute. Other visual records may be obtained to indicate the quantity and quality of pills 102.

In some embodiments, dispenser 110 accounts for each pill 102. For example, dispenser 110 counts each pill delivered to receptacle 112. In the embodiment of FIG. 2, dispenser 210 counts pills 102 that are removed from system 200 by separator 220. For example, dispenser 210 counts pills 102 delivered to receptacle 212 including the total number of pills 102 dispensed less any pills 102 removed by separator 220. In some embodiments, a calculation based on the rate and spacing of oriented pills 102 is used to determine the quantity of dispensed pills 102. For example, dispenser 210 spaces pills 102 to determine the number of pills 102 delivered to receptacle 212 per second and reduces the calculated value by the number of pills 102 removed by separator 220. In some embodiments, a counter is coupled to dispenser 210 and/or separator 220 to count pills 102 dispensed in receptacle 212 and/or removed from dispense path 206 by separator 220. As shown in FIGS. 1 and 2, images 118 and 218 of dispensed and/or removed pills 102 are stored in systems 100 and 200 to enable an operator to later identify pills 102. For example, an operator (e.g., pharmacist) identifies misplaced pills 102 in the batch of pills 102. For convenience only, the following description will refer to system 100 of FIG. 1, except where a separator 220 is used. It should be understood the following description applies equally to either system 100 of FIG. 1 or system 200 of FIG. 2.

Camera 116 is located about dispenser 110 and records pill parameters 104 as pills 102 traverse through dispenser 110 in a predetermined orientation and rate. Camera 116 is located about dispenser 110 such that camera 110 is located to a side, above, under, at an angle, and/or another orientation relative to dispenser 110. In various embodiments, system 100 utilizes a single camera 116 or a plurality of cameras 116 along and/or about channel 106. Camera 116 captures images 118 (e.g., visual data, characteristics, or indicia). The data captured is generally in the form of photographic images 118 (e.g., a single photographic image 118 or a frame from a plurality of photographs on a video image), but also includes other processed data modified and/or post-processed into an image 118 that is generated on display 122. For example, an infrared sensor generates visual images 118 on display 122 that are based on data signals of electromagnetic wavelengths outside the visible light spectrum (e.g., CMOS, CCD, NIR). Camera 116 may capture video at a fixed rate per second, e.g., 30 frames per second (FPS). Camera 116 may capture a single photograph, or a plurality of photographs, at a predetermined specified time. Camera 116 may capture images 118 based on an event, such as pill 102 traveling into a specific location, or on timing based on spacing and/or orientation of pills 102. Camera 116 captures any electromagnetic signal and/or other data to display as an image 118.

In some embodiments, camera 116 captures a video image 118 of each pill 102 in channel 106 to isolate pill parameters 104 of each pill 102 as dispensed pills 102 travel. Camera 116 and/or processor 114 use algorithms to determine which frame in video image 118 best captures identifying pill parameters 104 of pill 102. For example, system 100 checks every pill 102 with 30 pictures stitched together in one second (e.g., a 30 FPS video system with a feed rate of 1 pill/second). In some embodiments, system 100 uses a 120 FPS camera and stitches the frames for each pill 102. Frame rates include any range between 20 and 240 FPS, specifically between 30 FPS and 120 FPS. In some embodiments, system 100 uses the known orientation of pills 102 traveling at a predetermined rate through the system 100 to capture images 118 of pill parameters 104 at a known time and/or place. For example, camera 116 takes a photographic image 118 (or a series of images 118) of each pill 102. Camera 116 and/or display 122 render the images 118 (photo/video/data) in real time and/or store images 118 for future verification.

For purposes of this disclosure, camera 116 includes any sensor or device that captures a data signal (e.g., an image 118). Examples of camera 116 include a camcorder, an analog camera, a digital camera, a copier, a scanner, a multi-functional peripheral device, light sensors, and/or other cameras. In addition, camera 116 is not limited to visible light. In some embodiments, camera 116 detects electromagnetic signals of different wavelengths outside the visible spectrum. For example, detected wavelengths include, microwave, infrared, the spectrum of visible light, ultraviolet light, x-rays, gamma rays, and/or other wavelengths and spectrums. In some embodiments, camera 116 detects wavelengths of audio and/or radio waves.

In the embodiment of FIG. 2, separator 220 operates to remove pills 102 from system 200. Separator 220 removes pills 102 from dispense path 206 of dispenser 210 with pill parameters 104 outside of a threshold range. Separator 220 permits pills 102 with pill parameters 104 within the predetermined threshold to pass into receptacle 212. Separator 220 automates pill 102 removal from channel 106 prior to distribution of the pill 102 to receptacle 212. For example, separator 220 removes pill 102 from dispenser 210 when camera 216 captures image(s) 118 with pill parameters 104 of pill 102 that are evaluated by processor 214 and determined to exceed threshold limits. Processor 214 then signals separator 220 to remove pill 102 from dispense path 206 of dispenser 210. In some embodiments, pill parameters 104 are assigned a numeric value that classifies the tolerance for pill parameters 104 of each pill 102 in channel 106 of dispenser 210. For example, separator 220 classifies removed pills 102 based on a numeric value of pill parameters 104 outside the threshold.

Returning to FIG. 1, processor 114 is coupled to hopper 108, dispenser 110 (e.g., including channel 106), camera 116, separator 220, and/or display 122. Processor 114 receives and processes indicia signals and/or images 118 from camera 116 and generates and stores pill parameters 104 associated with one or more pills 102 dispensed at a time of the associated images 118. Processor 114 can return the images 118 to display 122 for human review, use algorithms, artificial intelligence, and/or deep learning to send diversion signals that indicate pills 102 outside a threshold value that are dispensed in receptacle 112. Processor 114 stores the recorded signals or images 118 associated with pill parameters 104 of each pill 102 in electronic memory 124 either internally and/or externally. And, in some embodiments, processor 114 sends diversion signals to separator 220 to automate removal when a pill parameter 104 is outside the threshold. In this configuration, separator 220 diverts pill 102 from channel 106.

Processor 114 captures, analyses, and/or verifies pill parameters 104 of each dispensed pill 102. For example, if a single pill parameter 104 does not meet the threshold, processor 114 generates a signal to display 122 and/or separator 220 to remove pill 102. In some embodiments, averaged threshold values determine whether pill parameters 104 meet the tolerance value. For example, pills 102 dispensed in receptacle 112 with some pill parameters 104 outside the threshold limit, but with a scaled (e.g., an average) numeric value of pill parameters 104 that is inside the threshold, may not generate a diversion signal. Thus, provided the average of some or all pill parameters 104 is within the threshold, pill 102 is not separated from channel 106. For example, an operator determines and sets the threshold limits for each pill parameter 104 or a set of pill parameters 104 that are analyzed collectively. System 100 discards removed and quarantined pills 102, and/or a human (e.g., pharmacist) manually evaluates the pill parameters 104 of the removed pills 102. For example, separator 220 removes and quarantines a broken pill 102 for later human evaluation. The human later discards the broken pill 102.

In another example, processor 114 identifies which receptacles 112 have pills 102 outside of a threshold, and a pharmacist or other operator manually evaluates display 122 of pills 102 in receptacle 112 and removes pills 102 outside the threshold or discards the confederate receptacle 112. In some embodiments, system 100 automatically determines and identifies receptacles 112 with pills 102 outside the threshold. In other embodiments, system 200 automatically disposes of broken and/or quarantined pills 102 that exceed the threshold. In other embodiments, separator 220 removes the broken pills 102 for human review and/or additional testing. Separator 220 tracks removed pills 102 so that they correlate to the verification images 118 taken by camera 116. In this way, systems 100 and 200 can store and retrieve verification images 118 corresponding to pills 102 outside the threshold) in receptacle 112.

With reference to FIGS. 1 and 2, each batch of pills 102 (e.g., identified by a unique NDC number) has different thresholds for different pill parameters 104. For example, an NDC number identifies a batch of pills 102 with a unique drug profile (e.g., predetermined pill 102 parameters and/or thresholds). The drug profile identifies a size, profile, the wavelength of reflected electromagnetic wavelengths (e.g., color), shape, dose, and/or other marks on the target batch of dispensed pills 102. The drug profile includes acceptable pill parameters 104 and thresholds, such that the threshold is stored and predetermined in the drug profile of pills 102 before system 100 operation. For example, pill 102 with a first NDC number has a ±5% threshold for size and a ±10% threshold for color on the RGB scale (Red, Green, Blue). A pill 102 with a second NDC number has a ±15% threshold for size and a ±7.5% threshold for color on the same RGB scale. In addition, pills 102 can use different photo-rendering techniques.

In some embodiments, LED lights provide a first pill 102 with a red appearance under LED light even though the first pill 102 appears white in natural light. Similarly, a second pill 102 appears blue under photo-rendering LED light even though under natural light the second pill 102 is green. Such LED photo-rendering enhances pill parameters 104 and makes the pill parameters 104 easier to identify. For example, photo-rendering enhances pill parameters 104 of a broken pill 102 making it easier to identify for removal. In some embodiments, photo-rendering emphasizes markers and/or doses marked on pills 102. The marker and/or dose appears black on a white pill 102 even though the colors naturally are the same under natural light. In this embodiment, LED photo-rendering enhances system's 100 ability to process image 118 and/or enhances future human visual inspection of image 118.

A combination of thresholds for RGB light defines whether a pill 102 is within the threshold or out of the threshold reflected color. For example, separator 220 assigns a threshold to the reflected light in an RGB scale for a particular batch of pills 102 (e.g., with a specific NDC number). A single threshold can apply to a composite of all the colors (e.g., Red, Green, and Blue). Alternatively, several thresholds may apply individually and differently to each reflected electromagnetic wavelength. In other words, the threshold may apply to a composite color with a combination of Red, Green, and Blue, and/or individually to each reflected color (e.g., Red, Green, or Blue). For example, processor 114 assigns separator 220 a ±10% threshold to the composite RGB value for a first pill 102. Processor 114 assigns separator 220 a ±10% threshold to the reflected red value, a ±5% threshold to the reflected blue value, and a ±7.5% threshold to the reflected green value. In some embodiments, the RGB values use LED photo-rendering to generate a tighter threshold for particular threshold values. System 100 can use alternative wavelengths of light. For example, infra-red light or ultraviolet light are used to enhance the pill parameters 104 and threshold limits for a particular pill 102. Processing and quarantining each batch of pills 102 depends on the particular properties of system 100 and pill 102. As such, the thresholds for one batch of pills 102 differ from another batch of pills 102 in the same environment. Alternatively, the threshold for a first pill 102 can utilize a different environment relative to the photo-rendering for a second pill 102 and each pill may have different thresholds within their respective environments.

System 100 stores and assigns threshold values for the size, shape, color, reflected electromagnetic waves, dose, markers, profile, and/or other pill 102 pill parameters 104 according to an assigned NDC number. In some embodiments, the operator assigns each parameter a threshold for a batch of pills 102 based on the NDC number. In some embodiments, the operator assigns threshold values for a batch of pills 102 based on visible pill parameters 104 of pill 102. In other embodiments, the pill dispensing system 100 stores and/or records pill parameters 104 with their accompanying threshold limits for the associated NDC number. For example, an operator enters the NDC number for a batch of pills 102 loaded into hopper 108 and system 100 automatically generates the pill parameters 104 and thresholds for each pill parameter based on pre-programmed information or past use.

In general, the threshold for each pill parameter 104 varies independently of other pill parameters 104. System 100 assigns each pill parameter 104 independent threshold limits. The thresholds can range from 1% to 50% for each pill parameter 104. For example, the threshold range is from zero to ±1%, 2%, 3%, 4%, 5%, 6%, 7%, 8%, 9%, 10%, 15%, 20%, 25%, 30%, 35%, 40%, 45%, or 50% of the target pill parameter 104 value. For example, processor 114 can assign a threshold value for the size of pill 102 that is ±5% of the target size for the pill 102 and a threshold value for the color that is ±10% the target RGB color for pill 102. Alternatively, processor 114 can assign pill 102 a +6% and −2% threshold for the target size, color, or other parameter. In other words, thresholds may have asymmetric ranges about a target threshold.

System 100 includes one or more processors or processors 114 that determine pill parameters 104 of a pill 102 based on images 118 as the pill 102 is dispensed into receptacle 112. Processor 114 processes the generated images 118 for each pill 102. The post-processed images 118 indicate pill parameters 104 of the dispensed pill 102 and the quantity of dispensed pills 102 into receptacle 112. Processor 114 counts pills 102 dispensed into receptacle 112 and archives image 118 verification associated with each pill 102. In various embodiments, processor 114 compares a dose and/or characteristic data of the recorded signals for each pill parameter 104 of the target pills 102 at a rate of at least 2.5 pills 102 per second, specifically at least 5 pills 102 per second, specifically at least 10 pills 102 per second, specifically at least 20 pills per second, and more specifically at least 30 pills per second. Processor 114 can archive image 118 for verification of each pill 102 quarantined by separator 220. Processor 114 may use an algorithm, artificial intelligence, and/or machine learning to recognize pills 102 distributed to receptacle 112 and/or those removed by separator 220. For example, processor 114 counts the quantity of pills 102 dispensed into receptacle 112 and automatically verifies each threshold pill parameter 104 for each pill 102 in receptacle 112. Processor 114 follows a similar process for removed or separated pills 102. Processor 114 renders this information (e.g., as image 118) on display 122 in real time and/or stores the information in memory 124 for future retrieval.

In some embodiments, processor 114 generates one image 118 for each pill 102 dispensed. The system 100, 200, and/or a pharmacist can then review the thresholds and pill parameters 104 for each pill 102 dispensed into receptacle 112. In some embodiments, processor 114 generates a plurality of images 118 for each pill 102 dispensed. In this configuration, processor 114 selects the best image 118 (e.g., a representative image 118) from the plurality of images 118 associated with each pill 102. Processor 114 stores image 118 for retrieval to enable a pharmacist to review each image 118. In some embodiments, processor 114 takes a plurality of images 118 each associated with a single pill 102 and specifically renders image 118 for the particular pill parameters 104. For example, system 100 renders one image 118 of pill parameters 104 in infrared light, another in blue light, and a third in ultraviolet light to highlight the pill parameters 104 of each pill 102. For each dispensed pill 102, processor 114 collects and stores several verification images 118. For example, a cover image 118 presents the pharmacist with a general overview of pill parameters 104 and when selected, processor 114 displays the plurality of photographic images 118, e.g., when the pharmacist double-clicks the cover image 118. Similar documentation and verification processes apply to quarantined pills 102 removed by separator 220.

In some embodiments, processor 114 stores predetermined pill parameters 104 and/or thresholds for NDC corresponding to the identification of particular pill 102. For example, an operator inputs pill parameters 104 for and NDC pill group, and processor 114 learns (through an algorithm, artificial intelligence, post-processing, machine learning, or deep learning/programming) pill parameters 104. In some embodiments, the operator inputs pill parameters 104, and processor 114 stores them for future use and/or accesses them in RAM. Processor 114 accesses electronic memory 124 to determine the stored pill parameters 104 corresponding to a particular NDC identified pill 102. Processor 114 accesses memory 124 to determine the specific thresholds for different pill parameters 104 of each NDC pill 102 identifier. Different pills 102 have different thresholds for each pill parameter 104 or feature. Processor 114 associates the NDC code with pill parameters 104 and thresholds of a particular group or batch of pills 102 (e.g., in a drug profile). Processor 114 then retrieves pill parameters 104 and/or threshold values from electronic memory 124 associated with the pill 102 when the operator provides the NDC identifier. Although processor 114 is shown in FIG. 1 as a part of camera 116, processor 114 can be located anywhere within system 100. For example, system 100 includes one or more processors 114 in display 122, dispenser 110, a separate device, the cloud, and/or in other locations.

Processor 114 described herein can be coordinated by operating system software, such as iOS, Android, Chrome OS, Windows 7, Windows 8, Windows Server, Windows CE, Unix, Linux, SunOS, Solaris, iOS, Blackberry OS, VxWorks, or other compatible operating systems. In other embodiments, a proprietary operating system may control the computing device. Conventional operating systems control and schedule computer processes for execution, perform memory management, provide file system, networking, I/O services, and provide a user interface functionality, such as a graphical user interface ("GUI"), among other things.

Processors 114 described herein may implement the techniques described herein using customized hard-wired logic, one or more Application Specific Integrated Circuits (ASIC) or Field Programmable Gate Arrays (FPGA), firmware and/or program logic which causes processors 114 to be a special-purpose machine. According to one embodiment, parts of the techniques disclosed herein are performed by processors 114 of FIG. 1 in response to executing one or more sequences of instructions contained in memory 124. Such instructions may be read into memory 124 from another storage medium, such as storage device. Execution of the sequences of instructions contained in memory 124 causes processor 114 to perform the process steps described herein. In alternative embodiments, hard-wired circuitry may be used in place of or in combination with software instructions.

Moreover, the various illustrative logical blocks and modules described in connection with the embodiments disclosed herein can be implemented or performed by a machine. Examples include a processor 114, a Digital Signal Processor 114 (DSP), an ASIC, an FPGA or another programmable logic device, discrete gate or transistor logic, discrete hardware components, or any combination thereof designed to perform the functions described herein. A processor/controller device or processor 114 can be a controller, microprocessor, microprocessor, or state machine or combinations of the same. Processor 114 includes electrical circuitry configured to process computer-executable instructions. In another embodiment, processor 114 includes an FPGA or another programmable device that performs logic operations without processing computer-executable instructions. Processor 114 can also be implemented as a combination of computing devices, e.g., a combination of a DSP and a processor 114, a plurality of processors 114, one or more processors 114 in conjunction with a DSP core, or any other such configuration. Although described herein primarily concerning digital technology, a processor 114 may also include primarily analog components. For example, some or all of the rendering techniques described herein may be implemented in analog circuitry or mixed analog and digital circuitry.

Processor 114 can store the processed images 118 in memory 124 and/or transmit the images 118 to a display 122. Display 122 indicates a visual representation of the recorded signal (e.g., image 118) indicative of pill parameters 104 for each pill 102 dispensed. Display 122 also indicates a quantity of pills 102 dispensed into receptacle 112. Processor 114 can transmit images 118 to display 122 in real time or on demand. Display 122 includes any device configured to receive images 118 and/or display or store images 118. In some embodiments, display 122 is located at or near system 100. In some embodiments, display 122 is remote from pills 102, hopper 108, channel 106, camera 116, separator 220, receptacle 112, and/or system 100. A remote display 122 configuration enables visual verification of pill parameters 104 and the number of dispensed pills 102 from a remote location (e.g., at another time and/or place). This access enables a pharmacist to verify pills 102 dispensed in a receptacle 112 remotely. In addition, display 122 includes an electronic memory 124 device (e.g., memory 124) that stores images 118 for future analysis and verification. As such, display 122 effectively documents images 118 for audits and verification reporting.

For example, processor 114 sorts and stores photograph images 118 that include pill parameters 104 and characteristics for each dispensed pill 102. Processor 114 sorts, stores, retrieves, and/or returns the photograph to visual display 122 where an operator visually verifies pill parameters 104 based on the visual indicia or photographic signal of each pill 102 during review of the imaged 118 pill parameters 104 shown on display 122.

Display 122 includes any device that receives a processed signal from camera 116 and includes a wide variety of electronic hardware. For example, display 122 includes, but is not limited to, a mobile phone (e.g., a smartphone), healthcare monitoring devices, electronics systems, webcams, a television, a computer monitor, a computer, a hand-held computer, a tablet computer, a laptop computer, a personal digital assistant (PDA), a digital video recorder (DVR), a multi-functional peripheral device, etc. Display 122 apparatuses can include unfinished products, lenses, and memory 124.

In system 100, memory 124 includes any non-transitory computer-readable storage medium. Although memory 124 is shown in FIG. 1 as a part of camera 116, memory 124 can be located anywhere within system 100. For example, system 100 can locate memory 124 in display 122, dispenser 110, a separate device, the cloud, and/or in other locations. Processor 114 may access memory 124 to correlate the NDC code with a particular pill 102. For example, the thresholds and pill parameters 104 corresponding to an NDC code can be stored in memory 124. These program instructions can reside in RAM memory, flash memory, ROM memory, EPROM memory, EEPROM memory, registers, hard disk, a removable disk, a CD-ROM, or any other form of a non-transitory computer-readable storage medium. Such special-purpose computing devices may also combine custom hard-wired logic, ASICs, or FPGAs with custom programming to accomplish the techniques. The special-purpose computing devices may include desktop computer systems, server computer systems, portable computer systems, handheld devices, networking devices or any other device or combination of devices that incorporate hard-wired and/or program logic to implement the techniques.

In some embodiments, receptacle 112 receives all distributed pills 102 from dispenser, and system 100 identifies potential pills 102 and/or receptacles 112 with pill parameters 104 outside a threshold. In other embodiments, receptacle 212 collects pills 102 after processor 214 determines that all pill parameters 104 are within the assigned threshold limits. If one parameter is outside the threshold, pill 102 may be separated (e.g., by separator 220) and removed from system 200 and not permitted into receptacle 212.

In one example, a 10,000 batch of pills 102 are loaded into hopper 108 and identified with an NDC number and a unique order number. The order number includes a load number and/or a group number identifying hopper 108 and/or receptacle 112 for pill 102. The NDC number is used to identify pill parameters 104 for evaluation. The unique order number, identifying this particular batch of 10,000 pills 102, may correspond to 333 thirty day supplies of pills 102 (e.g., 30 pills in 333 receptacles).

In various embodiments, receptacle 112 receives a 30 day, 60 day, 90 day, 365 day, etc. supply of pills. For example, a first receptacle 112 is removed from dispenser 110 after 30 or more pills (e.g., 1 month supply) are dispensed into the first receptacle 112. A second receptacle 112 is then coupled to the pill 102 dispenser 110 to collect additional dispensed pills 102 (e.g., a second 1 month supply of 30 pills). In various embodiments, other quantities are contemplated such as supplies for at least a 30 day, 60 day, 90 day, or 120 day supply. For example, the quantity of pills 102 dispensed into receptacle 112 corresponds to the quantity of pills 102 in a single prescription, such that pills 102 dispensed in receptacle 112 are sold directly to a patient with the prescription.

In this way, the first and second receptacles 112 collect pills 102 with indicia signals indicative of pill parameters 104 that are within the threshold or tolerance for pill 102. Receptacle 112 can then be sold directly to the patient or combined with other pills 102 and sold as a complete pharmaceutical package. In some embodiments, receptacles 112 are sold to pharmacies with their associated verification data and images 118, as described herein.

For example, in some embodiments, system 100 assigns each receptacle a unique batch number. The batch number assigned may include the NDC number, hopper 108 load number, and/or receptacle 112 group number. With this information, system 100 can locate the pertinent images 118 for each dispensed pill 102 in receptacle 112. For example, each image 118 in receptacle 112 is assigned a record of pill parameters 104 characteristic of the pill 102 data within receptacle 112 based on the unique batch number. The batch number may use a combination of the load number, the group number, and/or the NDC number to uniquely identify pills 102 contained in receptacle 112. Processor 114 assigns a unique batch number (e.g., comprising the NDC number and appended by a load number and group number) to receptacle 112 and associate the images 118 from camera 116 to the batch number. System 100 appends the batch number to the NDC identifier. Unique batch codes created sequentially or randomly uniquely identifies pills 102 and associated images 118 captured by camera 116. System 100 stores and retrieves images 118 of each dispensed pill 102 in receptacle 112 associated with that identifying assigned batch code.

Figure 3:
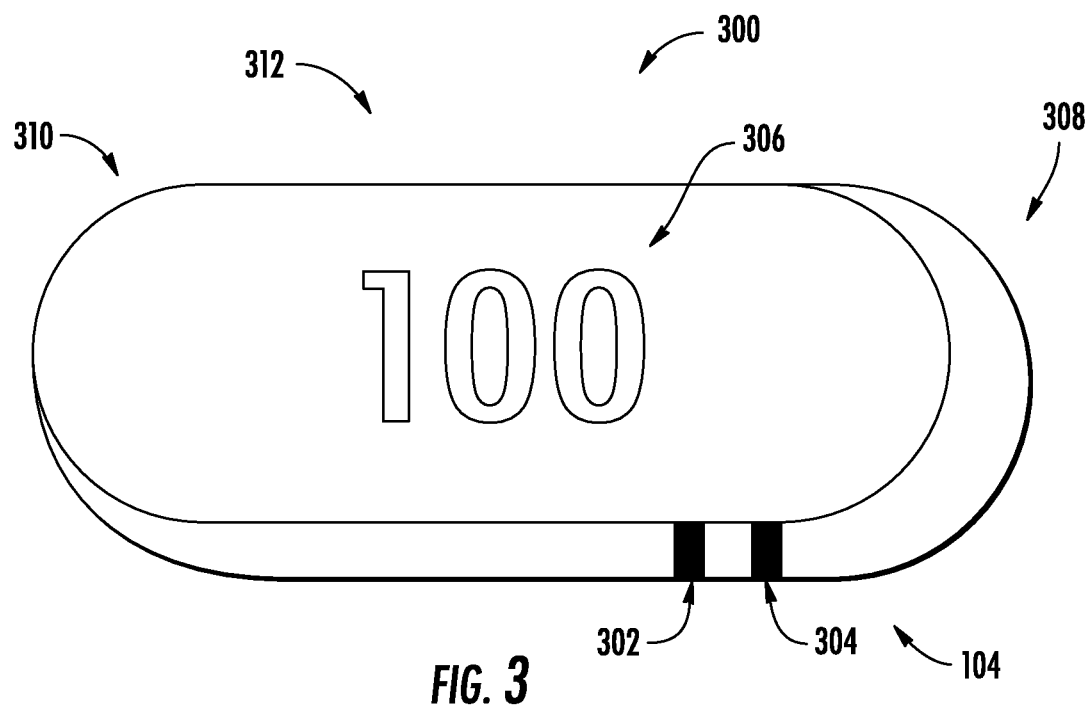
FIG. 3 is a detailed view of a pill illustrating various pill parameters such as size, markings, shape, and dose selected by the system and used to verify the dispensed pills.

FIG. 3 illustrates a generic pill 300 with various pill parameters 104. System 100 identifies (FIG. 1) and/or system 200 separates (FIG. 2) a batch of pills 300 according to pill parameters 104 such as markings 302 and 304, dose 306, profile shape 308, color 310, and size 312. As used in this application, color 310 refers to any detectable reflected electromagnetic wave, including wavelengths outside the visible spectrum, e.g., near infra-red (NIR), CMOS, CCD, etc. As illustrated in FIG. 3 these pill parameters 104 are used to verify pills 300 dispensed into receptacle 112. Pills 300 may be the same as, or similar to, pill 102 illustrated in FIGS. 1 and 2. Pill parameters 104 of pill 300 include identifying marks 302 and 304. For example, generic pill 300 includes a first mark 302 to identify a first pill 300 and a second mark 304 to identify a second pill 300. Two marks 302 and 304 on pill 300 differentiate pill 300 from a pill 102 with one mark (e.g., mark 302 only, not shown). Pill 300 includes a numeric inscription indicating the dose 306 (e.g., 100 mg). Pill 300 includes a pill parameter 104 for a profile shape 308.

In some embodiments, system 100 enhances the photo-rendering of the profile shape 308 of generic pill 300 with selected LED lights, colors or reflected electromagnetic waves. Photo-rendering enhances numeric indicators of dose 306 and/or other identifying marks 302 and 304. For example, system 100 includes LED lights, an LED camera, and/or visual, infra-red, or ultraviolet filters to enhance signals of pill parameters 104. Generic pill 300 has an associated color 310. The associated color 310 occurs natively under natural light, or system 100 renders the associated color or pill parameter 104 under LED or artificial light specifically selected for generic pill 300. One pill parameter 104 of pill 300 includes a size 312. For example, generic pill 300 differs from a second pill 102 based on pill parameters 104 indicated a size 312 of the respective pills 102 and 300. Photo-rendering system 100 enhances the illustration, record, identification, separation, and/or verification of the size 312 of pill 300 as it traverses, travels, or moves through system 100.

Figure 4:
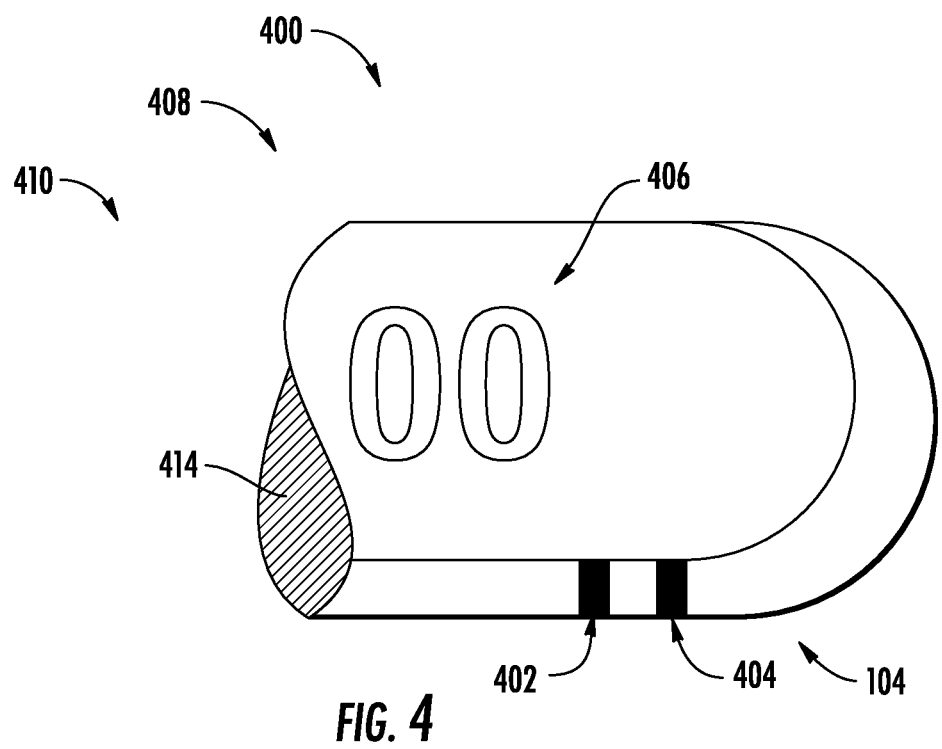
FIG. 4 is a broken pill with otherwise the same pill parameters as the pill in FIG. 3.

FIG. 4 illustrates a broken generic pill 400. Broken generic pill 400 may be the same as or similar to generic pill 300, except pill 400 is broken. For example, broken pill 400 has a first identifying mark 402 and a second identifying mark 404 indicating that broken pill 400 has the same NDC identifier as pill 300, as shown in FIG. 3. Depending on the location of the break, broken pill 400 may be missing a first 402 mark and/or a second mark 404. In this situation, the identity of pill 400 cannot be accurately determined based on a single pill parameter 104. Thus, system 100 analyzes each pill parameter 104 of pill 400 and analyzes pill 400 for breaks.

Similarly, depending on the location of the break, broken pill 400 may have an inscription indicating the same dose 406 (e.g., for a small break) or a partial dose 406 (e.g., for a large break, as illustrated). Because pill 400 is broken, pill 400 has a different profile shape 408. The different profile shape 408 can identify pill 400 in a receptacle 112 (FIG. 1) or for automatic removal by separator 220 to isolate pill 400 from receptacle 212 (FIG. 2). The broken generic pill 400 in FIG. 4 renders the same color 410 under LED and/or natural light as generic pill 300, but may show a different color 410 along broken area 414. In some embodiments, photo rendering enhances the color 410 of broken area 414 and/or the broken profile shape 408. For example, photo rendering enhances a small or undetectable broken area 414 of pill 400 for camera 116, processor 114, and/or display 122 enhancing the identification of pill 400 for later validation, separation, identification, and/or removal.

Figure 5:
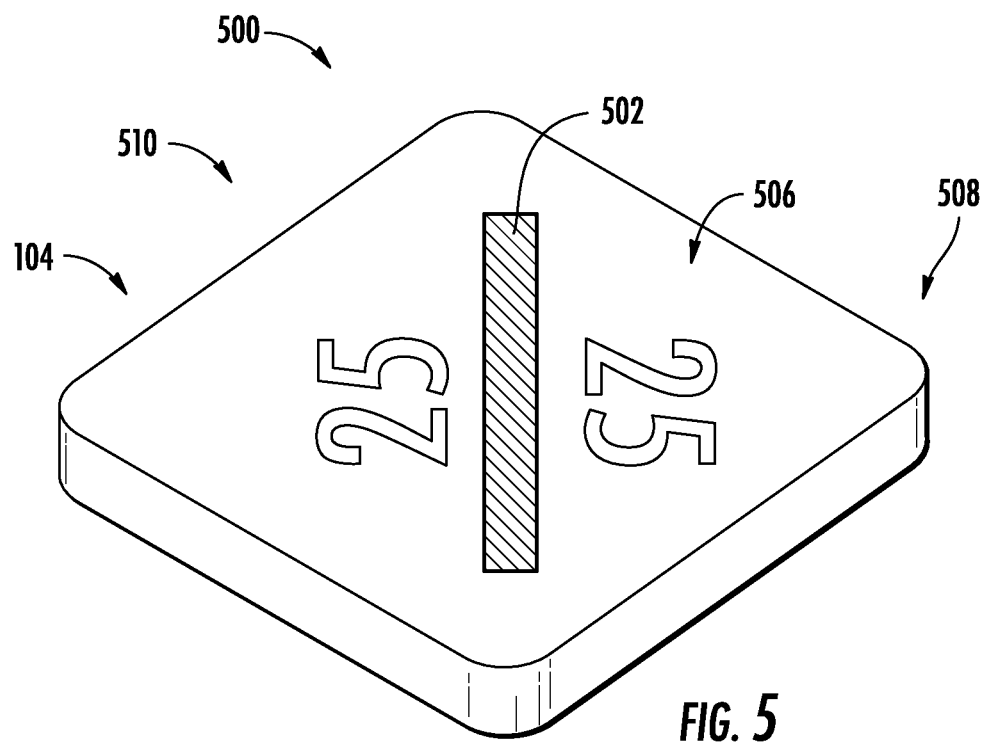
FIG. 5 is a different pill compared to FIG. 3 and illustrates different pill parameters, which are out of the thresholds for the pill parameters of FIG. 3.

FIG. 5 illustrates a different pill 500 with a unique NDC number. System 100 may identify and/or separate pill 500 from pill 300 based on one or more pill parameters 104 (e.g., see FIGS. 1 and 2). For example, pill 500 contains a single marker 502 and has a different dose 506 than pill 300. The profile shape 508 of pill 500 also contrasts with pill 300. In some embodiments, pill 500 has a different color 510 than pill 300. Although pill 500 is not broken, many pill parameters 104 contrast with pill 300. System 100 assesses the pill parameters 104 and determines whether to separate pill 500 based on these pill parameters 104. For example, if pill 500 were mixed in with pill 300 in hopper 108, camera 116 would identify the pill parameters 104 of pill 500 and/or separate pill 500 with separator 220 from the batch of pills 300 before it reaches receptacle 212. In some embodiments, system 100 does not include a separator 220. Instead, system 100 identifies receptacles 112 for verification when an out of threshold pill 500 is observed in dispenser 110 and/or deposited into receptacle 112.

Photo rendering and advanced processing enhance the detection processes of pill parameters 104. Moreover, if system 100 screens for pill 500, each pill parameter 104 would have a different threshold than pill parameters 104 corresponding to pill 300. Pill 500 includes different pill parameters 104 than pill 300. Since pill 300 and pill 500 each have a unique NDC number, system 100 identifies and assigns them each a drug profile with different pill parameters 104 and threshold limits.

Figure 6:
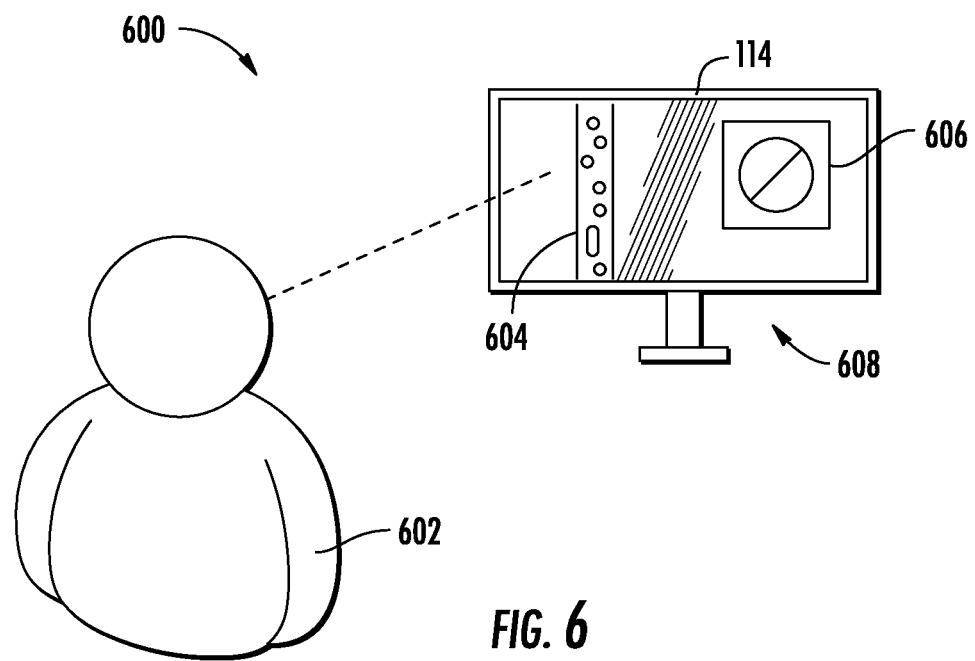
FIG. 6 is a visual inspection system within the system of FIG. 1, according to an exemplary embodiment.

FIG. 6 illustrates a visual inspection system 600 including a detailed view of display 122 within a pill dispensing system 100. Reference to FIGS. 1 and 5 demonstrates the visual inspection system 600 as a subset of the pill dispenser system 100, described in FIG. 1. An operator 602, e.g., a pharmacist, of the visual inspection system 600 can observe display 122 in real time or at a later time, after pills 102 are dispensed in receptacle 112. System 100 can locate system 600 within, near, or proximate to other features of system 100, as illustrated in FIG. 1. Alternatively, as illustrated in FIG. 6, visual inspection system 600 may relocate display 122 to a remote location that is removed from the other components of system 100. The operator 602 may inspect a collective image 604 of the group of pills 102 traversing along a dispense path or track of dispenser 110. The collective image 604 can be a video or photograph of a series of pills 102 oriented along the dispense path of dispenser 110. A reference image 606 shows video, frames, photographs or other images 118 of pill 102 dispensed and identified in the collective image 604.

In some embodiments, the reference image 606 includes a cover photo of pill 102. When selected by the operator 602, the cover photo may open a series of images 118 associated with pill 102. Images 118 can include video of pill 102 at different locations along the dispense path of dispenser 110 or a series of photographs either as separated/individual frames of a video image or from a succession of photographs taken by camera 116. In some embodiments, operator 602 opens a plurality of pill 102 images 118 associated with different pills 102. In this way, operator 602 compares pill parameters 104 of one pill 102 along dispenser 110 with a reference image 606. Display 122 is configured to also show receptacle 112 and include a numerical count for each pill 102 deposited into receptacle 112. Thus, system 600 enables visual verification that the correct pills 102 were dispensed into receptacle 112 at the correct quantity.

In some embodiments, display 122 includes other GUI rich features such as operator 602 notations associated with pill 102 images 118. In some embodiments, operator 602 viewing pills 102 in real time interacts with display 122 to interface with processor 114. For example, operator 602 inspects a suspect pill 102 on the dispense path of dispenser 210 and uses processor 214 to isolate pill 102 into separator 220. In some embodiments, operator 602 temporarily isolates pill 102 for later detailed inspection and either returns pill 102 to dispenser 210, receptacle 212, and/or separator 220 depending on the outcome of the later detailed inspection.

Display 122 also operates on stored data pertaining to a batch of previously dispensed pills 102. For example, display 122 communicates with processor 114 to access memory 124 and load a batch of pills 102 identified by the NDC number, the load number, and the group number, etc. Operator 602 then observes the historical data of the dispensed pills 102 in receptacle 112. System 100 and/or 600 enable audit documentation to provide verification that unique receptacle 112 received the correct quantity and quality (within tolerance) of pills 102.

Figure 7:
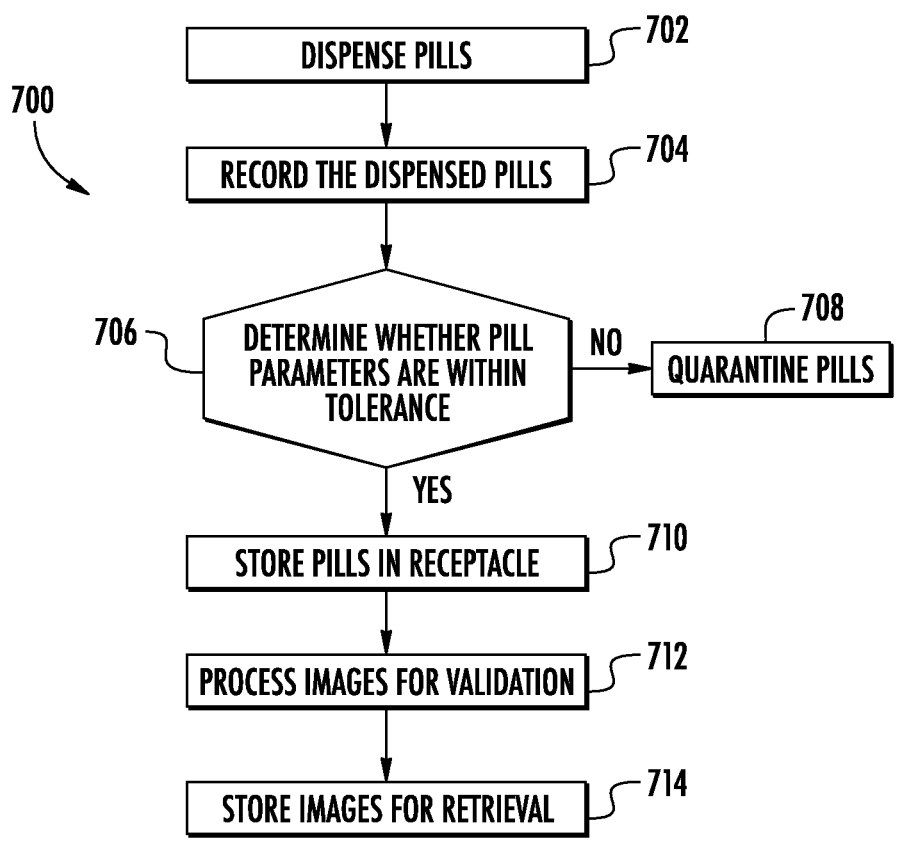
FIG. 7 is a schematic of a method of separating and verifying the pills.

FIG. 7 shows a method 700 of verifying pills dispensed or collected into receptacle 112. Method 700 includes a first step 702 of dispensing pills 102 into a vibratory channel 106 that orients pills 102 in a predetermined distance relative to adjacent pills 102 in channel 106. Step 704 includes recording a signal indicative of pill parameters 104 of the pills 102 dispensed into channel 106. Step 704, identifies and/or optionally removes pills 102 with pill parameters 104 outside a threshold value, based on the predetermined set of pill parameters 104. Step 706 processes the signals representative of the pills 102 dispensed into receptacle 112. Step 706 associates recorded signals for each pill dispensed into receptacle 112. Step 708 involves quarantining pills 102 outside the threshold value. Pills 102 within the threshold values are stored in step 710 and an image 118 corresponding to each pill 102 is stored in step 704. Step 712 validates the signal indicative of both the quantity of dispensed pills 102 and the image 118 representative of the pill parameters 104. Step 712 may also determine the accuracy of the predetermined threshold values to remove pills 102 outside the threshold values for that batch of pills 102 (e.g., identified by the NDC code). In step 714, images 118 are processed and stored for future retrieval and verification. Step 714 may include storing images 118 for both quarantined pills in step 708 and/or dispensed pills in step 710.

In some embodiments, pill parameters 104 used in step 606 include a size, shape, color, reflected electromagnetic wavelength, marks, and/or numerical dose associated with the drug profile related to a unique NDC code for the target pills 102. The drug profile includes predetermined pill parameters 104 and threshold values for the dispensed pills 102. In some embodiments, image 118 is a photographic image 118 of each dispensed pill 102 that identifies and compares each pill parameter 104 to a threshold value for the drug profile of dispensed pill 102.

In the disclosure provided above, apparatus, systems, and methods for feedback and control of a pill dispensing system are described in connection with particular exemplary embodiments. It is understood, however, that the principles and advantages of the embodiments can be used for any other systems, apparatus, or methods with a need for feedback and control responsive to an indication of visual pill parameters 104. Although certain embodiments are described with reference to an example camera sensor, it will be understood that the principles and advantages described herein can be applied to other types of sensors. While some of the disclosed embodiments may be described with reference to analog, digital, or mixed circuitry, in different embodiments, the principles and advantages discussed herein can be implemented for different parts as analog, digital, or mixed circuitry. Moreover, while some schematics are provided for illustrative purposes, other equivalent schematics can alternatively be implemented to achieve the functionality described herein.

Unless the context clearly requires otherwise, throughout the description and the claims, the words "comprise," "comprising," "include," "including," and the like are to be construed in an inclusive sense, as opposed to an exclusive or exhaustive sense; that is to say, in the sense of "including, but not limited to." Where the context permits, words in the Detailed Description using the singular or plural number can also include the plural or singular number, respectively. The words "or" in reference to a list of two or more items, is intended to cover all of the following interpretations of the word: any of the items in the list, all of the items in the list, and any combination of the items in the list. All numerical values provided herein are intended to include similar values within a range of measurement error.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example, ±6%, ±10%, ±16%, etc.). Unless stated otherwise, all measurements are at standard conditions including ambient temperature and pressure.

It should be understood that the figures illustrate the exemplary embodiments in detail, and it should be understood that the present application is not limited to the details or methodology set forth in the description or illustrated in the figures. It should also be understood that the terminology is for the purpose of description only and should not be regarded as limiting.

Further modifications and alternative embodiments of various aspects of the disclosure will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, reflected electromagnetic wavelengths, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes, and omissions may also be made in the design, operating conditions and arrangement of the various exemplary embodiments without departing from the scope of the present disclosure.

While the current application recites particular combinations of, various embodiments of the disclosure relate to any combination of any of the features described herein whether or not such combination is currently claimed, and any such combination of features may be claimed in this or future applications. Any of the features, elements, or components of any of the exemplary embodiments discussed above may be used alone or in combination with any of the features, elements, or components of any of the other embodiments discussed above.

What is claimed is:
1. A pill dispenser, comprising:
   a hopper including pills;
   a channel that orients and moves the pills from the hopper, wherein the channel orients a plurality of the pills via vibration to a similar orientation relative to other pills in the channel;
   a camera situated about the channel that records an image of each of the pills;
   a processor coupled to the camera, the processor configured to compare the image of each of the pills to a parameter associated with the pills; and
   a separator coupled to the channel, wherein the separator removes the pill from the channel when the respective image is outside a threshold with respect to the param- eter and does not remove the pill from the channel when the respective image is within the threshold with respect to the parameter.

2. The pill dispenser of claim 1, wherein the parameter is selected from a group consisting of a size, color, and shape of the pills.

3. The pill dispenser of claim 1, wherein the parameter corresponds to a National Drug Code (NDC) that identifies the pills.

4. The pill dispenser of claim 1, wherein the separator is configured to remove a broken pill from the channel.

5. The pill dispenser of claim 1, comprising an LED light and a wavelength filter to enhance visibility of the image recorded for each of the pills.

6. The pill dispenser of claim 1, wherein the image of each pill is a first image of each pill, and wherein the camera records a plurality of images of each pill, including the first image, and wherein the plurality of images are recorded in different wavelengths with respect to each other.

7. The pill dispenser of claim 1, comprising a display configured to display the image of each pill.

8. The pill dispenser of claim 1, wherein the processor is configured to compare the image for each pill for at least 100,000 pills per hour.

9. The pill dispenser of claim 1, wherein the threshold comprises a first threshold, and wherein the separator is configured to compare the image with respect to the first threshold below the parameter and a second threshold above the parameter, and wherein the second threshold is greater than the first threshold.

10. A pill dispenser, comprising:
a hopper including a plurality of pills;
a belt that orients and moves the pills from the hopper, the belt including a plurality of pockets, each of which are configured to receive a single pill of the plurality of pills;
a camera situated about the belt that records an image of each of the pills;
a processor coupled to the camera, the processor configured to compare the image of each of the pills to a parameter associated with the pills; and
a separator coupled to the belt, wherein the separator removes the pill from the belt when the respective image is outside a threshold with respect to the parameter and does not remove the pill from the belt when the respective image is within the threshold with respect to the parameter.

11. The pill dispenser of claim 10, wherein the parameter is selected from a group consisting of a size, color, and shape of the pills.

12. The pill dispenser of claim 10, wherein the parameter corresponds to a National Drug Code (NDC) that identifies the pills.

13. The pill dispenser of claim 10, comprising a display configured to display the image of each pill.

14. The pill dispenser of claim 10, wherein the image comprises a stitched image generated from a video.

15. The pill dispenser of claim 14, wherein the video was recorded under multiple wavelengths.

16. A pill dispenser, comprising:
a hopper including a plurality of pills;
a channel that orients and moves the pills from the hopper, the channel including a plurality of pockets each configured to receive a single pill of the plurality of pills;
a camera situated about the channel that records an image of each of the pills;
a processor configured to determine whether the image is within a first threshold of the first parameter, and determine whether the image is within a second threshold of the second parameter, wherein the second threshold is different than the first threshold; and
a separator coupled to the channel, the separator removes the pill from the channel when the image is outside the first threshold with respect to the first parameter or the image is outside the second threshold with respect to the second parameter, and wherein the separator does not remove the pill from the channel when the image is within the first threshold with respect to the first parameter and the image is within the second threshold with respect to the second parameter.

17. The pill dispenser of claim 16, wherein the first parameter and the second parameter are each selected from a group consisting of a size, a profile, a dose, and a measured wavelength of each pill of the plurality of pills.

18. The pill dispenser of claim 16, wherein the first parameter corresponds to a size of each pill of the plurality of pills and the second parameter corresponds to a color of each pill of the plurality of pills.

19. The pill dispenser of claim 16, wherein the first parameter corresponds to a first color of each pill of the plurality of pills and the second parameter corresponds to a second color of each pill of the plurality of pills, wherein the second color is distinct from the first color.

20. The pill dispenser of claim 16, comprising a wavelength filter to enhance visibility of the image recorded for each of the pills.

* * * * *